(12) United States Patent
Scarffe

(10) Patent No.: US 6,324,911 B1
(45) Date of Patent: Dec. 4, 2001

(54) APPARATUS AND METHOD FOR DETECTING AN INTERFACE

(75) Inventor: Michael Frederick Scarffe, Little Horwood (GB)

(73) Assignee: Whitlenge Drink Equipment Limited, Halesowen (GB)

(*) Notice: Subject to any disclaimer, the term of this patent is extended or adjusted under 35 U.S.C. 154(b) by 0 days.

(21) Appl. No.: 09/600,189

(22) PCT Filed: Jan. 12, 1999

(86) PCT No.: PCT/GB99/00092

§ 371 Date: Nov. 2, 2000

§ 102(e) Date: Nov. 2, 2000

(87) PCT Pub. No.: WO99/36750

PCT Pub. Date: Jul. 22, 1999

(30) Foreign Application Priority Data

Jan. 13, 1998 (GB) .................................................. 9800533

(51) Int. Cl.$^7$ .................................................. G01N 29/06
(52) U.S. Cl. ............................ 73/627; 73/629; 73/290 V; 73/597; 73/602
(58) Field of Search .................................. 73/627, 290 V, 73/291, 64.53, 61.69, 61.75, 69.53, 651, 629, 620, 597, 602

(56) References Cited

U.S. PATENT DOCUMENTS

| 4,595,131 | * | 6/1986 | Ruskin et al. ........................ 222/640 |
| 4,748,846 | * | 6/1988 | Haynes ................................ 73/290 V |
| 5,085,077 | * | 2/1992 | Stapleton et al. ................... 73/290 V |
| 5,095,748 | | 3/1992 | Gregory et al. .................... 73/290 V |
| 5,095,754 | * | 3/1992 | Hsu et al. ............................... 73/602 |
| 5,471,872 | | 12/1995 | Cummings .......................... 73/290 V |
| 5,603,363 | * | 2/1997 | Nelson ................................. 141/351 |
| 5,627,310 | | 5/1997 | Johnson .............................. 73/64.53 |
| 5,765,433 | | 6/1998 | Johnson .............................. 73/290 V |
| 6,053,042 | * | 4/2000 | Hwang et al. ..................... 73/290 V |

FOREIGN PATENT DOCUMENTS 04 188 394   7/1992   (JP) ................................. G07F/13/00

* cited by examiner

Primary Examiner—Hezron Williams
Assistant Examiner—Jacques Saint-Surin
(74) Attorney, Agent, or Firm—Ohlandt, Greeley, Ruggiero & Perle, LLP

(57) ABSTRACT

Apparatus for detecting an interface (13) between two media of a heterogeneous system, comprising transmission means (21) to send a signal through one medium from the transmission means (21) to the interface (13), measuring means (32b, 32c, 32d) to measure the time taken for the signal to be reflected to a reception means (36), and processing means (40c, 40d) to use said time to determine the distance of the interface from the transmission means.

10 Claims, 3 Drawing Sheets

APPARATUS AND METHOD FOR DETECTING AN INTERFACE

DESCRIPTION OF INVENTION

This invention relates to an apparatus and method for detecting an interface, and particularly but not exclusively for detecting an interface between separate phases of a heterogeneous system, such as, for example, an interface between a liquid and a gas, or a liquid and a solid.

The invention is particularly directed at detecting an interface between water and a gas above the level of the water, whereby to detect the level of water in (e.g.) a container, and/or an interface between water and ice, such as are found in beverage coolers/carbonators.

Conventionally in beverage coolers/carbonators a probe has been used to monitor the level of the liquid. Such probes typically comprise means to measure the conductivity of the medium in which the probe is immersed, from which measurement of the depth of the probe covered by the liquid may be determined. However the conductivity of water varies considerably between different geographic regions, and indeed, some types of water contain so few free ions that the conductivity is extremely difficult to detect.

Additionally, beverage coolers/carbonators usually comprise a bank of cooling medium such as ice, located within a chamber in which the potable liquid is cooled. The depth of the bank of ice varies in accordance with the demand placed on the system, and it is thus desirable to monitor the depth of the ice bank so that the amount of refrigerant which is caused to flow to the ice bank may be controlled as appropriate.

It has however hitherto been extremely difficult to monitor the depth of the ice bank satisfactorily.

According to a first aspect of the invention, there is provided apparatus for detecting an interface between two media of a heterogeneous system, comprising transmission means to send a signal through one medium to the interface, measuring means to measure the time taken for the signal to be reflected to a reception means, and processing means to use said time to determine the distance of the interface from the transmission means.

If desired the transmission means and the reception means may be located adjacent to one another, but conveniently the transmission means and the reception means are coincident.

Conveniently the apparatus comprises a wave guide, the transmission means being provided by a transducer located at one end of the wave guide, said wave guide passing through, and containing, said one medium.

Thus, conveniently, the wave guide extends from a position below a chamber containing said one medium to a position at or beyond the interface.

Preferably the apparatus comprises a datum disposed in the same medium as that through which the signal is sent, and measuring means adapted to measure the time taken for a signal to be reflected from the datum to the or a further reception means Said measuring means may be the measuring means which measures the time taken for the first said signal to be reflected, and the or a further processing means may be utilized to determine the velocity of the signal in the medium, and hence the distance of the interface from the transmission means, in dependence upon the measured time.

Conveniently the wave guide comprises reflecting means operative to reflect a signal from the transmission means to a second interface, such as between water and ice within said chamber. Advantageously, the reflecting means is also operative to reflect a reflected signal from the second interface to the reception means.

Thus the reflecting means may be provided adjacent to a section of the waste guide which is open or substantially transparent to the signal.

In this way by the use of the or a further processing means, the thickness of a bank of ice within the chamber may be determined.

According to this invention there is also provided a beverage cooler and/or carbonator incorporating apparatus as set out above.

According to this invention there is also provided a method of detecting an interface between two media of a heterogeneous system, comprising sending a signal through one medium from a transmission position to the interface, measuring the time taken for the signal to be reflected to a reception position, and using the time taken to determine the distance between the transmission position and the interface.

Conveniently, the time taken is utilized to calculate the temperature of a liquid phase of the system.

Preferably, the signal comprises an ultrasound wave.

The method is particularly suitable for detecting an interface between a liquid and a gas, such as water and air/carbon dioxide, as is found in beverage coolers/carbonators.

The transducer is preferably constructed from a material such as polyvinyl-difluorodine, conveniently covered with a thin layer of stainless steel to protect it and to provide a good ground connection.

The invention will now be described by way of example by reference to the accompanying drawings, wherein.

Figure 1:
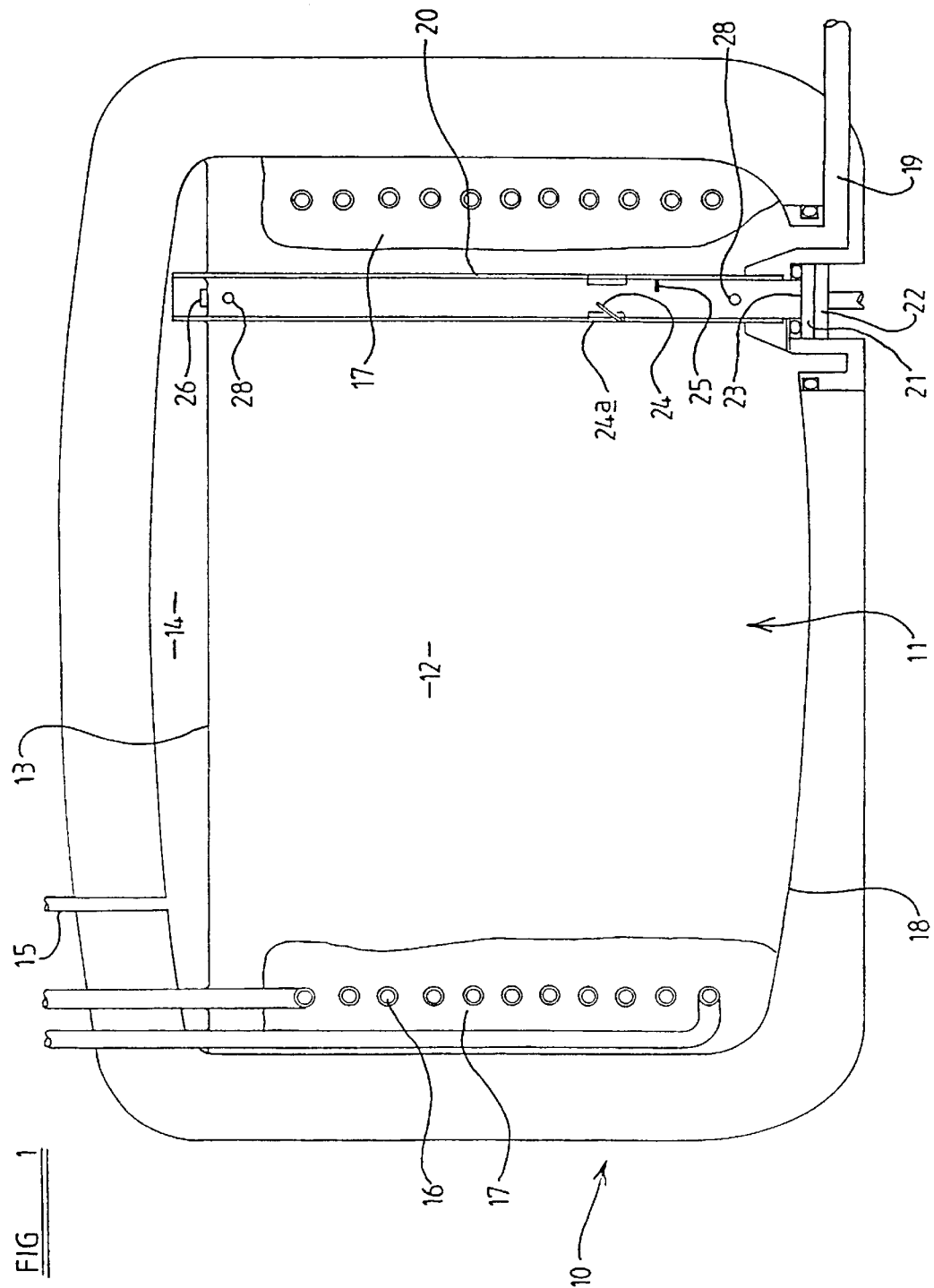
FIG. 1 is a cut away view of a beverage cooler/carbonator in accordance with the present invention.

Referring now to FIG. 1, there is shown a beverage cooler/carbonator 10, comprising a chamber 11 in which is contained a quantity of liquid (for example carbonated water) 12, having an upper level 13. Above the level 13, there is maintained a quantity of pressurized gas, conveniently carbon dioxide, 14, supplied to the chamber through gas inlet 15. The upper level 13 of the liquid 12 thus defines an interface between the liquid and the gas located thereabove.

The chamber further comprises one or more cooling elements 16, through which refrigerant flows, to cause ice 17 to form around the inside of the wall or walls 18 of the chamber.

Thus, a state of equilibrium is obtained whereby carbonated water, free carbon dioxide, and ice (in fact conveniently frozen carbonated water) co-exist in the chamber.

As is conventional with such beverage coolers/carbonators, cold carbonated water is withdrawn from the chamber 11 through an outlet 19, and passed to a dispensing head (not shown).

The apparatus comprises means for monitoring the level of the water, and the thickness of the ice bank, in the form of an ultrasonic wave guide 20, extending from a position below the chamber, to a position above the level 13 of the water.

The wave guide 20, conveniently a stainless steel cylindrical tube, is adapted to transmit an ultrasonic signal from an ultrasonic transducer 21, which is operative on application of an electric current to a printed circuit board (PCB) 22, and which is protected by a thin stainless steel plate 23.

The transducer 21 also functions as a receiver; operative to detect a reflected signal, and to apply in consequence an output signal to a processor.

The wave guide is provided with a reflector 24, conveniently in the form of a mirror or polished metal plate, which is angled conveniently at approximately 45°, to reflect an ultrasonic signal away from the axis of the wave guide, towards the ice bank 17.

The signal may exit the wave guide through a transparent region or window 24a in its periphery, or there may simply be provided a small aperture in the periphery.

Additionally, the reflector 24 is also operative to reflect a signal which is reflected by the ice bank 17, back down the wave guide to the transducer 21.

The inside of the wave guide is also provided with a generally planar datum 25, which is located in the path of the ultrasonic signal emitted by the transducer, and arranged to reflect the signal back down the wave guide.

The precise distance of the planar datum from the transducer is known, such that by measuring the time taken for a signal reflected from the datum to arrive back at the transducer, the velocity of the signal in the medium (here, carbonated water) may be obtained, from which tile height of the water level in the chamber 11 may be calculated.

Moreover, as the velocity of sound, including ultrasound, varies in accordance with the temperature of the liquid through which it passes, an accurate measurement of the temperature of the liquid may also be obtained.

Thus, in use, an electric current is caused to flow to the PCB 22, which causes an ultrasound signal to be emitted up through the wave guide, part of which is incident on the datum, part of which is incident, and reflected by, the reflector 24, and part of which continues up through the wave guide towards the interface between the water and carbon dioxide, defined by the upper level 13 of the water.

By use of electronic circuitry which is arranged so that the transducer 21 may also convert the reflected signal into a weak electric signal, the time taken for the signal a) to reach the ice, and b) to reach the water/gas interface, may be determined accurately.

By use of the datum, the velocity of the signal through the water may also be determined, and the distance of the ice and interface respectively from the transducer may therefore be accurately obtained.

In this way, when a predetermined lower level of water is detected, means may be operative to refill the chamber, up to but not exceeding a predetermined upper level, with the result that the chamber does not run dry and does not overfill.

Moreover, as the distance of the ice from the reflector 24 is monitored, refrigerant may be caused to flow through the cooling elements 16 when it is determined that the "death" of ice has reached a predetermined minimum and flow of the refrigerant may similarly be caused to cease when the depth of ice reaches a predetermined maximum.

It is envisaged by the applicants that there may additionally be provided a loose fitting float 26 in the wave guide 20, which may be used to provide an improved reflective surface to determine the position of the water/gas interface. Additionally, conveniently small holes 28 are provided in the wave guide 20 to permit circulation of the liquid therein.

Figure 2:
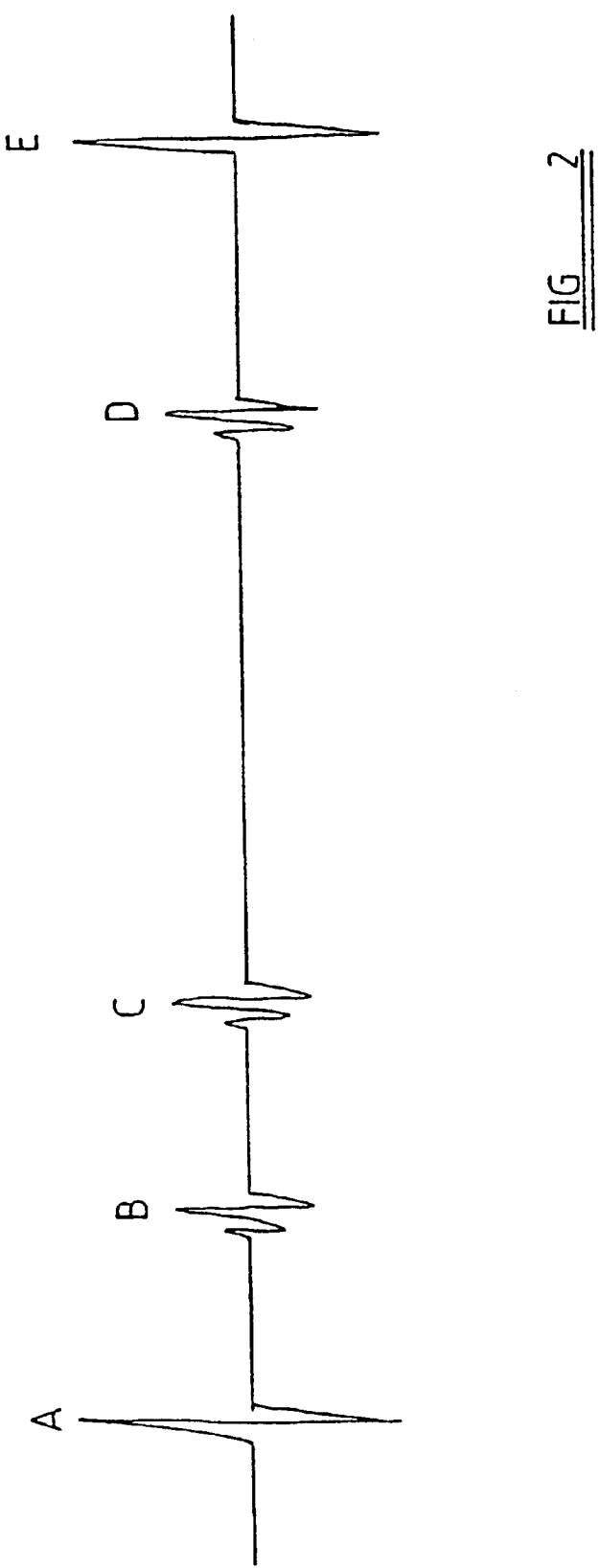
FIG. 2 is a typical trace which would be observed upon monitoring emitted and reflected signals using the apparatus shown in FIG. 1.

Referring now to FIG. 2, there is shown a sample trace which could be obtained by use of the apparatus shown in FIG. 1. Pulse A represents tile first emission of a signal from the transducer 21, and signal B corresponds to a reflection from the datum 25.

By measuring the time between these two signals, the velocity of the ultrasound in the medium concerned may be calculated, as the distance from the transducer to the datum is known.

Moreover, the temperature of the medium concerned may be obtained using readily available calibration curves, as the velocity of the signal depends upon the temperature of the medium.

Pulse C represents a reflected signal from the ice bank 17, and, as the velocity of the signal is known, and the time taken for the signal to reach the ice bank may be determined, the distance of the ice bank from the reflector 24 may be obtained, giving an accurate indication of the thickness of ice formed around the cooling elements 16.

Pulse D represents a reflected signal from the water/gas interface, the distance of which from the transducer may also be obtained using a process analogous to that explained above in relation to the ice thickness.

If desired, the process may be repeated, for reasons of accuracy, the next emission of an ultrasound signal being illustrated at pulse E.

Figure 3:
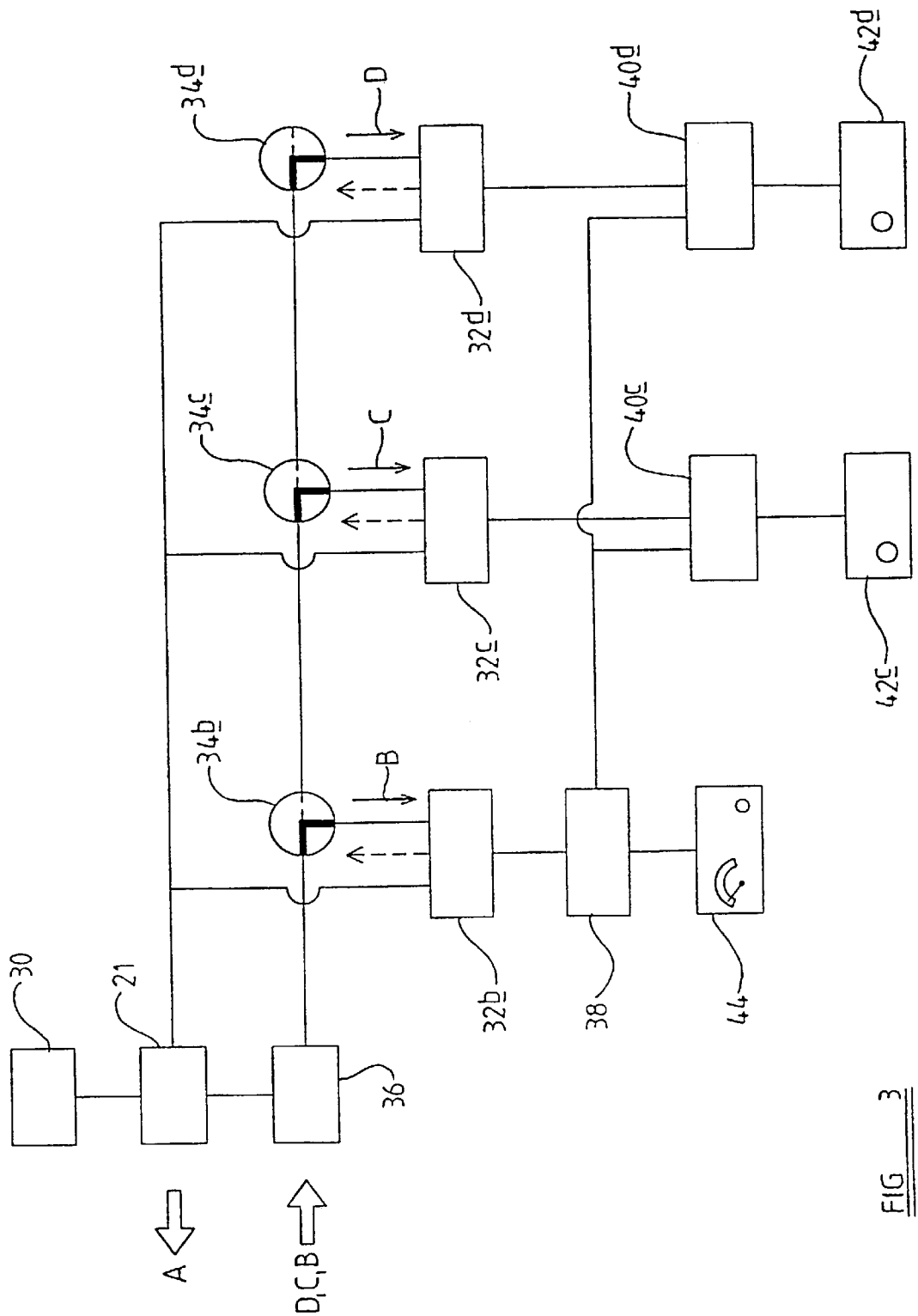
FIG. 3 is a schematic view illustrating a control mechanism of the apparatus.

FIG. 3 shows in schematic form a control means of the apparatus, by which the precise level of the water surface in the container, and the precise thickness of the ice bank, together with the temperature of the water in the container, may be determined.

An enable signal, which may be transmitted automatically at predetermined time intervals, and/or manually, is produced at generator 30 to trigger the transmitter (transducer 21) which, in addition to the Pulse A hereinbefore described, provides an input signal to each of three counters 32b 32c and 32d associated with the datum, the front face of the ice bank, and the surface of the water in the container, respectively, to cause said counters to commence operation.

When the first reflected signal B is received by receiver 36, a signal is generated by receiver 36 which is transmitted by switch 34b to datum counter 32b to terminate operation of the datum counter and to transmit a time signal to velocity measurement processor 38, which produces an output signal applied to two position processors 40c and 40d, associated respectively) with the front face of the ice bank and the surface of the water in the container.

Simultaneous with the transmission of the received signal to the counter 32b, a signal is transmitted to reset switch 34b.

Thus when the second reflected signal C is received by the receiver 36 (relating to the front face of the ice bank) a signal is generated by the receiver and transmitted through switch 34b and by switch 34c to counter 32c to terminate operation of the counter 32c causing a time signal to be fed to processor 40c.

In conjunction with the velocity signal received by processor 40c from processor 38, a position signal, representing the position of the front face of the ice bank, is fed to output controller 42c, at which it is compared with a preset, desired value: if the position signal indicates a thickness of ice bank less than that desired, the comparator may operate to supply further refrigerant to the cooling coils 17.

Simultaneous with the transmission of the received signal to the counter 32c, a signal is transmitted to reset switch 34c, and thus the third reflected signal D is applied via switches 34b, 34c and 34d to counter 32d to terminate operation thereof, resulting in a time signal being fed to processor 40d.

By the use of the velocity measurement signal obtained from processor 38, a distance signal is produced by processor 40d which is fed to comparator 42d. If the distance indicated by the signal from processor 40d is less than a preset, desired value input to comparator 42d (indicating a level of liquid in the container below that desired) an enable signal may be produced by comparator 42d to cause further water to flow into the container, until the signal produced by the processor 40d rises to a level above that preset into comparator 42d, indicating the attainment of a desired maximum level.

Simultaneous with the application of a signal to processor 40d, counter 32d is operative to reset all three switches 34b, 34c and 34d to their start positions, shown in FIG. 3.

Additionally, an output from processor 38 is applied to temperature processor 44, which provides an output indicating the temperature of the liquid in the chamber, and which may operate as a safety control.

It will of course be appreciated that separate receivers may be utilized to detect the reception of a signal reflected from the interface being measured, enabling self-contained measuring means 32, and/or processing means 38, 40, 42 to be utilized.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

What is claimed is:

1. A beverage dispensing apparatus comprising:
   a) a chamber in which a quantity of water may be contained,
   b) an outlet through which water may be drawn from said chamber, and
   c) an inlet extending into said chamber through which water may flow into said chamber, wherein the beverage dispensing apparatus comprises detection means to detect the position of an interface between at least a first and second media within said chamber, the detection means comprising:
      i) transmission means to transmit a signal through a wave guide comprising a single tubular construction, wherein said wave guide is disposed within said chamber such that said signal passes through said first medium toward said second medium;
      ii) reception means to detect a signal reflected from said interface between said first and second media;
      iii) a datum surface located in said wave guide at a known distance from the reception means;
      iv) timing means to measure a first time taken for a transmitted signal to be reflected by said interface back to said reception means and to measure a second time taken for a transmitted signal to be reflected from said datum surface to said reception means; and
      v) calculating means operative to determine the position of said interface in said chamber in accordance with said first and second measured times, and said known distance.

2. An apparatus according to claim 1 wherein said transmission means and said reception means are coincident.

3. An apparatus according to claim 1 wherein said signal is produced by a transducer located at one end of said wave guide which passes through, and contains, at least first said medium.

4. An apparatus according to claim 3 wherein the wave guide extends from a position below said chamber comprising at least first said medium to a position at or beyond said interface.

5. An apparatus according to claim 1 wherein said interface is between the surface of water in said chamber and pressurized gas in said chamber and pressurized gas in said chamber.

6. An apparatus according to claim 5 comprising control means operative to control the supply of water in response to the determined interface position.

7. An apparatus according to claim 1 wherein the second interface is between water in said chamber and a third medium which is the surface of a bank of ice in the chamber.

8. An apparatus according to claim 7 comprising control means operative to control the supply of refrigerant to said apparatus in response to said second determined interface position.

9. An apparatus according to claim 7 wherein said apparatus comprises means to detect the position of said second interface between at least said first and third media in said chamber, said timing means being operative to measure a third time taken for a transmitted signal to be reflected from said second interface to said reception means, and the calculating means being operative to determine the position of said second interface in said chamber in accordance with said second and third measured times, and said known distance.

10. An apparatus according to any one of claims 6, 8 and 9 wherein said control means is operative to determine temperature of the water in said chamber with reference to said measured times and said known distance.

* * * * *